United States Patent
Yamamoto et al.

(12) 
(10) Patent No.: US 6,512,148 B1
(45) Date of Patent: Jan. 28, 2003

(54) PROCESS FOR THE PRODUCTION OF BISPHENOL A

(75) Inventors: Susumu Yamamoto, Yokohama (JP); Atsumi Kukidome, Yokohama (JP); Makoto Nomura, Yokohama (JP); Keiji Maehara, Yokohama (JP); Kenji Nagahama, Kawasaki (JP)

(73) Assignee: Mitsubishi Chemical Corporation (JP)

( * ) Notice: Subject to any disclaimer, the term of this patent is extended or adjusted under 35 U.S.C. 154(b) by 0 days.

(21) Appl. No.: 09/937,401

(22) PCT Filed: Aug. 31, 1999

(86) PCT No.: PCT/JP99/04724

§ 371 (c)(1), (2), (4) Date: Sep. 26, 2001

(87) PCT Pub. No.: WO00/59853

PCT Pub. Date: Oct. 12, 2000

(30) Foreign Application Priority Data

Mar. 31, 1999 (JP) ............................................. 11-092554

(51) Int. Cl.⁷ ............................................... C07C 37/68

(52) U.S. Cl. ........................................ 568/724; 568/728
(58) Field of Search ................................. 568/727, 728, 568/724

(56) References Cited

U.S. PATENT DOCUMENTS 4,876,395 A * 10/1989 Kissinger
5,008,470 A * 4/1991 Powell
5,091,591 A * 2/1992 Cipullo
5,324,867 A * 6/1994 Asaoka

FOREIGN PATENT DOCUMENTS

EP 0 523 931 A2 10/1992
JP 2000-327614 * 11/2000

* cited by examiner

*Primary Examiner*—Michael L. Shippen
(74) *Attorney, Agent, or Firm*—Lorusso & Loud

(57) ABSTRACT

A process for the production of bisphenol A, including providing a melt of a crystalline adduct of bisphenol A and phenol, contacting the melt with a cation donating solid to neutralize the strong acid therewith, and then heating the melt to vaporize and remove phenol from the melt.

3 Claims, 1 Drawing Sheet

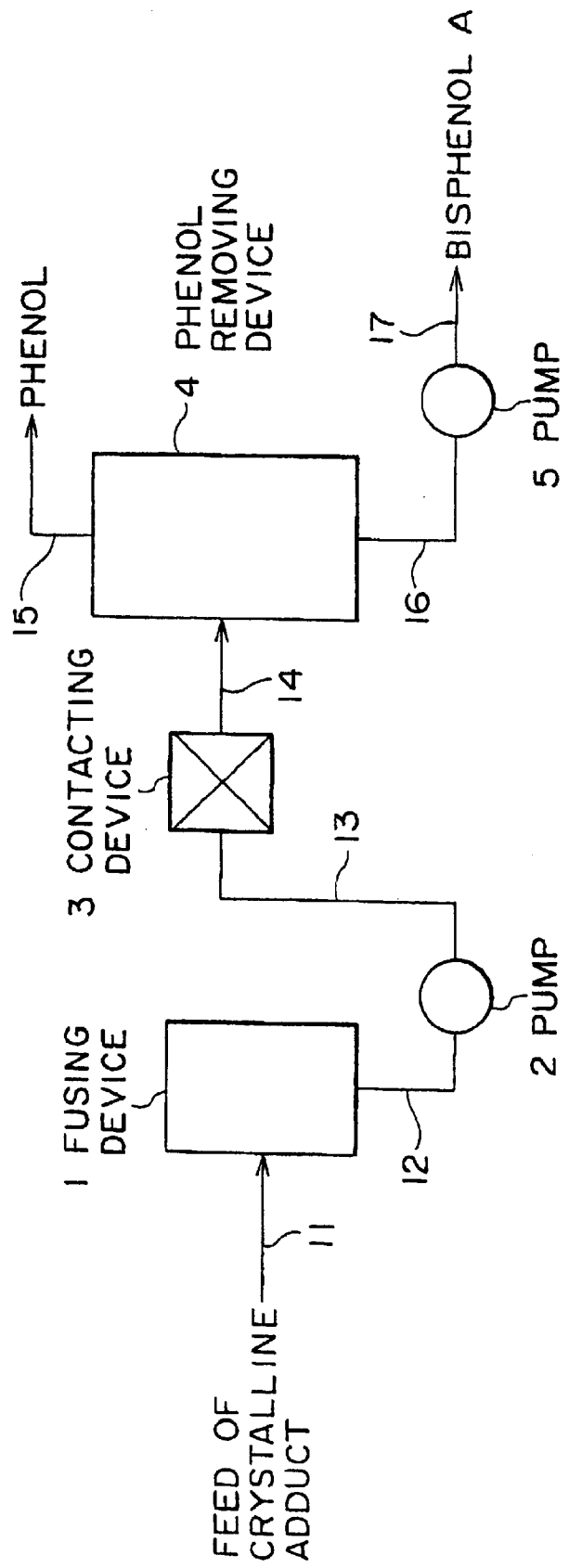

140
PROCESS FOR THE PRODUCTION OF BISPHENOL A

TECHNICAL FIELD

This invention relates to a process for the production of high purity bisphenol A.

BACKGROUND ART

One known method of producing bisphenol A (2,2-bis(4'-hydroxyphenyl)propane) includes reacting acetone with excess phenol in the presence of a strong acid catalyst such as a sulfonic acid-type cation ion exchange resin. The product is generally cooled to form crystals of an adduct of bisphenol A with phenol (hereinafter referred to simply as "crystalline adduct"). The crystalline adduct is collected and is then subjected to a phenol removing treatment to obtain a high purity bisphenol A. The phenol removing treatment is generally performed by heating a melt of the adduct to vaporize and separate phenol using, for example, a distillation tower.

It has been found that during the phenol removing treatment, bisphenol A is thermally decomposed to form impurities such as phenol and isopropenyl phenol. The decomposition of bisphenol A proceeds not only in the phenol removing device but also in a line downstream of the phenol removing device through which bisphenol A separated is discharged for recovery. It has also been found that it is difficult to avoid the decomposition of bisphenol A in the phenol removing step by mere control of the conditions of the phenol removing step.

The present invention has been made in view of the above problem.

DISCLOSURE OF THE INVENTION

The present invention provides a process for the production of bisphenol A, comprising providing a melt of a crystalline adduct of bisphenol A and phenol which contains a strong acid contaminant, and heating said melt to vaporize and remove phenol from the melt, characterized in that, before said heating, said melt is contacted with a cation donating solid to neutralize the strong acid contaminant therewith.

It has been found that thermal decomposition of bisphenol A during the phenol removing treatment is ascribed to the presence of a strong acid contaminant such as sulfuric acid or sulfonic acid in the crystalline adduct. The strong acid contaminant is considered to be derived from the strong acid catalyst used for the reaction of acetone with phenol.

The amount of the strong acid contaminant in a melt of the crystalline adduct is generally 0.003 meq/liter or less, typically 0.0001–0.001 meq/liter. By contacting the melt with a cation donating solid, such a trace amount of the strong acid contaminant has been found to be effectively neutralized in a stable manner irrespective of variation of the amount of the acid contaminant. With a liquid alkaline substance, it is impossible to neutralize such trace amount of a strong acid in a stable manner.

Any cation donating solid may be used for the purpose of the present invention as long as the strong acid contaminant can be neutralized therewith or converted into a substance, such as a salt, which no longer exhibits properties of a strong acid.

Examples of cation donating solids include cation exchange resins (such as —COOM type where M is a cation), inorganic ion exchangers (such as silicate (e.g. zeolite or silicalite) substituted by a cation), ceramics (e.g. glass and porcelain) containing an alkali metal oxide (e.g. $Na_2O$) and/or alkaline earth metal oxide (e.g. CaO), alkali metal compounds and alkaline earth metal compounds. The cation donating solid may be in any desired shape such as powder, granule (pellet), fiber, plate, porous plate, film, sheet or cylinder.

As the cation, there may be used alkali metal ions, such as sodium ions, potassium ions or lithium ions; alkaline earth metal ions, such as calcium ions or magnesium ions; ammonium ions; and organic ammonium ions derived from organic amines.

The contact of a melt of the crystalline adduct with the cation donating solid may be carried out in any desired method such as a packed tower method in which the melt is passed through a packed tower containing the cation donating solid, a filtration tower method in which the melt is passed through a filtration tower containing a layer of the cation donating solid, a dispersing method in which powder of the cation donating solid is dispersed in the melt, or a immersion method in which a molded body of the cation donating solid is immersed in the melt. Through the contact of the melt with the cation donating solid, the strong acid contaminant in the melt is neutralized by ion exchange reaction with the cation on surfaces of the solid.

The present invention will now be described in more detail below with reference to the accompanying drawing, in which FIG. 1 is a flow chart diagrammatically illustrating a device useful for carrying out the process of the present invention.

Referring to FIG. 1, a feed of a crystalline adduct of bisphenol A and phenol or a feed of phenol containing the crystalline adduct is introduced through a line 11 into a fusing device 1 where the feed is heated at 100–150° C., preferably 120–130° C., to melt or liquify the crystalline adduct and to form a melt (or a liquified adduct).

The melt is then passed through lines 12 and 13 and a pump 2 to a contacting device 3 where the melt is contacted with a cation donating solid contained therein, so that a strong acid contaminant in the melt is neutralized with the cation donating solid. The thus treated melt is then fed through a line 14 to a phenol removing device 4, such as a distillation tower or a thin film-type evaporator, where the melt is heated at 160–220° C., preferably 180–200° C., to vaporize and separate phenol from the melt. The vaporized phenol is withdrawn overhead from the phenol removing device through a line 15, while the bisphenol A is discharged through a line 16 and a pump 5 and is fed to a succeeding step such as granulation device (not shown) through a line 17.

The following example will further illustrate the present invention.

EXAMPLE 1

Using the device as shown in FIG. 1, bisphenol A was produced from a crystalline adduct. The operation conditions are summarized below.

Line 11:
  Feed: crystalline adduct in phenol (in the form of slurry); weight ratio of bisphenol A/phenol: 60:40
Line 12:
  Temperature of melt: 120° C.
  Concentration of strong acid: 0.001 meq/liter
Contacting device 3:
  Cation donating solid: a filter made of a glass fiber containing $Na_2O$ and CaO Line 14:

Temperature of melt: 150° C.

Concentration of strong acid: not detected

Line 16:

Temperature of bisphenol A: 190° C.

Concentration of phenol: 5–10 ppm by weight

COMPARATIVE EXAMPLE 1

Example 1 was repeated in the same manner as described except that the contacting device 3 was not used. Thus, the melt discharged from the fusing device 1 was directly fed to the phenol removing device 4. The results are as follows.

Line 14:

Temperature of melt: 150° C.

Concentration of strong acid: 0.001 meq/liter

Line 16:

Temperature of bisphenol A: 190° C.

concentration of phenol: 40–50 ppm by weight

What is claimed is:

1. A process for the production of bisphenol A, comprising:

providing a melt of a crystalline adduct of bisphenol A and phenol which contains a strong acid;

contacting said melt with a cation donating glass fiber to neutralize the strong acid therewith; and then heating said melt to vaporize and remove phenol from the melt.

2. A process as claimed in claim 1, wherein said cation donating solids include cation exchange resins, inorganic ion exchangers, ceramics, alkali metal compounds and alkaline earth metal compounds.

3. A process as claimed in claim 2, wherein said cation is selected from alkali metal ions, alkaline earth metal ions, ammonium ions and organic ammonium ions.

* * * * *